United States Patent
Kwak et al.

(10) Patent No.: US 6,395,947 B1
(45) Date of Patent: May 28, 2002

(54) METHOD FOR PREPARING DIARYLETHANE

(75) Inventors: Byong Sung Kwak; Seung Gweon Hong; Tae Jin Kim, all of Taejon (KR)

(73) Assignee: SK Corporation, Seoul (KR)

(*) Notice: Subject to any disclaimer, the term of this patent is extended or adjusted under 35 U.S.C. 154(b) by 0 days.

(21) Appl. No.: 09/600,301

(22) PCT Filed: Jan. 15, 1999

(86) PCT No.: PCT/KR99/00027

§ 371 (c)(1),
(2), (4) Date: Jul. 11, 2000

(87) PCT Pub. No.: WO99/36377

PCT Pub. Date: Jul. 22, 1999

(30) Foreign Application Priority Data

Jan. 15, 1998 (KR) .............................................. 98-1061

(51) Int. Cl.[7] .......................... C07C 15/067; C07C 1/20
(52) U.S. Cl. ........................................ 585/447; 585/469
(58) Field of Search .................................. 585/447, 469

(56) References Cited

U.S. PATENT DOCUMENTS 5,453,555 A   9/1995   Chang et al. ................ 585/469

FOREIGN PATENT DOCUMENTS

| EP | 753498 | 1/1997 |
| JP | 4931652 | 3/1974 |
| JP | 6242938 | 2/1987 |
| JP | 63238028 | 4/1988 |
| JP | 42257530 | 9/1992 |

*Primary Examiner*—Alan Siegel
(74) *Attorney, Agent, or Firm*—Abelman, Frayne & Schwab

(57) ABSTRACT

A method for preparing diarylethane is disclosed. Alkylation is carried out in a continuous type process at 100–300° C. under a pressure of 1–45 kg/cm² G in the presence of a solid acid catalyst while a reactant mixture comprising alpha-methylbenzylalcohol and at least one aromatic hydrocarbon at a volume ratio of 1:1–10, is fed at a weight hourly space velocity of 0.1–10 $h^{-1}$. The alpha-methylbenzylalcohol acts as an ailylating agent. Diarylethane can be prepared at a low cost, but a high production yield by the method.

7 Claims, No Drawings

METHOD FOR PREPARING DIARYLETHANE

This application is a 371 of PCT/KR99/00027 filed Jan. 15, 1999.

1. Technical Field

The present invention relates to a method for preparing 1,1-diarylethane (hereinafter referred to as "DAE") at a low cost with a high yield. More particularly, the present invention relates to the use of alpha-methylbenzylalcohol (hereinafter referred to as "MBA") in preparing DAE in a continuous type process, whereby the production cost can be reduced, but the production yield can be enhanced.

2. Background Art

DAE, which is characteristically colorless, odorless and nontoxic, is a high boiling point solvent. For example, diphenylethane is 220° C. in boiling point. Particularly, phenylxylylethane (hereinafter referred to as "PXE"), which is usually used as a solvent for dissolving wet-coloring agents for pressure-sensitive paper, is a useful compound as a plasticizer and heat transfer oil when processing plastics. For these reasons, effective and economical preparation methods of diarylalkanes which can give good product quality, such as PXE, have been required.

Various methods for preparing diarylalkanes, such as PXE, have been well known to the art. Of them, general is the reaction of alkyl benzene fractions containing 6–9 carbon atoms in the presence of a catalyst with styrene acting as an alkylating agent. Based on the catalyst employed, this technique is classified largely into the following two categories.

A first technique is to use conc. sulfuric acid as a catalyst, as disclosed in Japanese Pat. Laid-Open Pub. Nos. Hei 4-257530 and Sho 48-97858. This technique has an advantage of yielding relatively high quality products, but allows production processes in batch type only, because sulfuric acid is a homogeneous catalyst. Further, sulfuric acid requires a facility for isolating reaction products from the homogeneous catalyst and extorts after-treatments, such as acid neutralization and washing. Furthermore, use of sulfuric acid leaves problems to be solved in practice, including facility corrosion and waste water pollution.

In order to restrain the side reaction in which styrene monomers are converted into styrene oligomers, a large molar ratio of the styrene is monomers to the aromatic hydrocarbons, for example, 1:10 is needed when using the homogeneous catalyst. In addition, the catalyst should be fed at a weight as twice as that of styrene. The use of a large amount of the catalyst is disadvantageous in many aspects, for example, a reactor with a large volume and an increase in reclaim cost, so that the technique using sulfuric acid is inadequate to mass-production.

A second technique is as described in Japanese Pat. Laid-Open Pub. Nos. Sho 49-31652 and 63-238028, characteristic of using heterogeneous solid acid catalysts. The technique of using heterogeneous solid acid catalysts to react styrene with alkyl benzene has neither difficulty in catalyst isolation nor the problem of facility corrosion. However, it shows low production yield comparing to the techniques using homogeneous catalysts. Further, the second technique should be operated at a low styrene ratio because of side-products such as styrene oligomers. Examples of the heterogeneous solid acid catalysts include Y-type zeolite (Japanese Pat. Laid-Open Pub. No. Sho 63-238028) and active clay (Japanese Pat. Laid-Open Pub. No. Sho 49-31652). However, these two prior arts are of batch type. A continuous type process is also known as disclosed in Japanese Pat. Laid-Open Pub. No. Sho 62-42938 which uses a cation exchange membrane as a solid acid catalyst, but nowhere is mentioned catalyst life.

In result, upon preparing DAE by the alkylation of aromatic hydrocarbons, conventional techniques in which to use styrene as an alkylating agent are difficult to carry out in a continuous type process and have difficulty in using solid acid catalysts, even if they are convenient to isolate and reclaim, because of the production of a large quantity of styrene oligomers and of the low production yield ascribed to a low styrene fraction in the reaction. Use of sulfuric acid as a catalyst with the aim of obtaining a high production yield may cause facility corrosion and environmental pollution, so that corrosion-resistant facilities and an additional acid waste treatment process are required.

DISCLOSURE OF THE INVENTION

The intensive and thorough research on a method for preparing DAE, repeated by the inventors, resulted in the finding that use of MBA as an alkylating agent in the presence of a solid acid catalyst selected from synthetic or natural zeolites, such as Y type zeolite, X type zeolite, zeolite β, modernite, L type zeolite, ZSM-5, ZSM-11, ZSM-18, ZSM-12, mazzite and offretite, MCM-41, KIT-1, KIT-2, AIKIT-3, clay, and silica-alumina, can enhance the production yield of and the selectivity for DAE and allow the overall reaction process to be executed in a continuous process as well as a batch process.

It was also found that, when DAE was prepared on the basis of the above research, the conversion of MBA and the selectivity for DAE are both high even under the condition of high mole fraction of MBA in reaction materials and that the operability of the preparation in a continuous reactor significantly reduces the production cost.

The present invention is based on the above findings.

Therefore, it is an object of the present invention to overcome the above problems encountered in prior arts and to provide a method for preparing DAE at a high conversion rate and production yield with economical favorableness.

In accordance with the present invention, the above object could be accomplished by a provision of a method for preparing DAE, in which alkylation is carried out at a temperature of 100–300° C. under a reaction pressure of 1–45 kg/cm$^2$ G in the presence of a solid acid catalyst while a reactant mixture comprising alpha-methylbenzylalcohol as an alkylating agent and at least one aromatic hydrocarbon at a volume ratio of 1:1–0, is fed at a weight hourly space velocity of 0.1–10 h$^{-1}$.

In accordance with one aspect of the present invention, the solid acid catalyst is selected from the group consisting of Y type zeolite, X type zeolite, zeolite beta(β), modernite, L type zeolite, ZSM-5, ZSM-11, ZSM-18, ZSM-12, mazzite, offretite, MCM-41, KIT-1, KIT-2, AIKIT-3, clay, and silica-alumina.

BEST MODES FOR CARRYING OUT THE INVENTION

The present invention is characterized in that MBA, instead of styrene, is used as an alkylating agent. As a result of the intensive and extensive research of the inventors, the novel alkylating agent was observed to be much more advantageous in an economical aspect than the conventional one. MBA is an intermediate in the process of producing styrene monomers and can be obtained by oxidizing ethyl benzene. No particular limits are levied on the purity of MBA and the MBA which contains acetophenone at an amount of 15% may be used.

In the present invention, DAB is prepared from aromatic hydrocarbons with MBA serving as an alkylating agent. Examples of the aromatic hydrocarbons available include one or more selected from the group consisting of benzene, toluene, ortho-xylene, meta-xylene, para-xylene, ethyl benzene and trimethyl benzene. No particular limits are levied on the conditions of aromatic hydrocarbons, such as purity. Particularly preferable are aromatic hydrocarbon individuals isolated from the refomates when executing conventional petrochemical processes, or the mixtures thereof.

In accordance with the present invention, a useful catalyst is a kind of a solid acid catalyst selected from the group consisting of zeolites, for example, Y type zeolite, X type zeolite, zeolite beta (Higgins, et al., Zeolites Vol. 8, 1988, p446), modernite, L type zeolite, ZSM-5 (U.S. Pat. No. 3,702,886), ZSM-11 (Fyfe, et al., J. Am. Chem. Soc. vol. 111, 1989, p2470), ZSM-18 (Lawton, et al., Science, vol. 247, 1990, p1319), ZSM-12 (LaPierre, et al., Zeolites, vol. 5, 1985, p346), mazzite (D. W. Breck and G. W. Skeels, U.S. Pat. No. 4,503,023, 1985) and offretite (D. W. Breck, Zeolites Molecular Sieves, Wiley, 1974, p103), MCM-41, KIT-1, KIT-2, AlKIT-3, clay, and silica-alumina. These exemplified solid acid catalysts may be used as powder or in a molded form. As for the Y type zeolite, X type zeolite and modernite catalysts, they may be natural or synthesized. MCM-41, KIT-1, KIT-2 and AlKIT-3, available in the present invention, are mesoporous molecular sieves. KIT-1 is structured to have channels interconnecting in a three dimensional disordered way. The MCM-41 used in the present invention was prepared on the basis of the content of J. Am. Chem. Soc, 1992, vol. 115., p 10834, to Beck et al. and Preparation Example I disclosed in Korean Pat. Appl'n No. 97-41469 filed by the applicant. KIT-1 was prepared in the way disclosed in Example I of Korean Pat. Appl'n No. 96-52841 filed by the applicant while KIT-2 was prepared according to Example IV of the same patent application. AlKIT-3 was prepared in the way described in Example IX of Korean-Pat. Appl'n No. 97-6051 filed by the applicant. Where the catalyst has a form, alumina or silica may be added at an amount of 10–80 weight % upon molding. No restraint resides in the shape of the catalyst.

Now, a description will be given of the reaction conditions under which DAE is prepared by the alkylation of aromatic hydrocarbons with MBA in the presence of the catalyst, below.

Temperatures for the reaction may be varied depending on other conditions, but preferably ranges from 100 to 300° C. and more preferably from 120 to 270° C. For example, if the reaction is carried out at a temperature higher than 300° C., a serious side-reaction attributable to the self-reaction of MBA occurs and much coke is produced, leading to the reduction of catalyst life span and the decrease of production yield. On the other hand, at a temperature lower than 100° C., it is difficult for the alkylation to occur. Prior to the alkylation, the catalyst is preferably dried in an inert gas atmosphere. 100–120° C. is suitable for drying the catalyst.

As for reaction pressure, it is on the order of 1–45 kg/cm$^2$ G and preferably 2–40 kg/cm$^2$ G. Higher pressures than 45 kg/cm$^2$ G causes a serious side reaction ascribed to the self-reaction of MBA. On the other hand, lower pressures than 1 kg/cm$^2$ G makes it difficult to execute the alkylation in a continuous manner in an immobilized bed reactor. The gas suitable for maintaining the reaction pressure is selected from argon (Ar), nitrogen ($N_2$), hydrogen $(H)_2$ and the mixtures thereof and there are no particular limits on the condition for the gas, such as purity.

In the reactant mixture used, the volume ratio of the aromatic hydrocarbons to the alkylating agent, that is, MBA, is on the order of 1–10:1 and preferably 2–8:1. For example, if the volume ratio is larger than 10, the production yield of PXE decreases. On the other hand, the volume ratio lower than 1 causes coke to occur on the catalyst, resulting in the reduction of catalyst life span and the decrease of production yield.

As for the weight hourly space velocity ($h^{-1}$) of the reactant mixture of MBA and aromatic hydrocarbons, it ranges from 1 to 10 and preferably from 2 to 8.

A better understanding of the present invention may be obtained in light of the following examples which are set forth to illustrate, but are not to be construed to limit the present invention.

EXAMPLE 1

30 g of pelletized H-Beta (CP-811-BL25, commercially available from PQ) was charged into a 316 stainless steel fixed bed reactor (550 mm×50 mm OD). The reactor was heated to 110° C. under 0.20 SLPM (standard liter per minute) Argon flow at a pressure of 2 kg/cm$^2$ G. A mixture of xylene:MBA=5:1 was used as a reactant feed.

After drying the catalyst, argon was fed at a velocity of 0.20 SLPM to form a pressure of 20 kg/cm$^2$ at a temperature of 200° C. and, under this condition, reaction was carried out as feeding the reactant mixture at a weight hourly space velocity of 4.5 $h^{-1}$.

After 40 hour reaction, the product was analyzed by gas chromatography equipped with a flame ionization detector. The analysis showed that the average conversion of MBA was 100.0% and the average production yield of PXE was 86.21 wt %.

The conversion of MBA and the selectivity for PXE were calculated according to the following Equations 1 and 2, respectively:

$$\text{Conversion (\%) of } MBA = \frac{\text{Weight of } MBA \text{ reacted}}{\text{Weight of } MBA \text{ used}} \times 100 \quad \text{[Equation 1]}$$

$$\text{Selectivity (\%) for } PXE = \frac{\text{Wt. of } PXE \text{ converted from } MBA}{\text{Wt. of all products converted from } MBA \text{ reacted}} \times 100 \quad \text{[Equation 2]}$$

EXAMPLE 2

The same procedure as that of Example 1 was repeated, except that the silica-alumina (commercially available from Aldrich) extruded to pellet forms in a well known process was used as a catalyst for 250 hours. Gas chromatography analysis showed that the conversion rate of MBA was 100.0% and the selectivity for PXE was 68.04 wt %.

EXAMPLES 3 TO 6

The same procedure as that of Example 1 was repeated, except that Na-Beta (commercially available from PQ), Y type zeolite (CBV-780, commercially available from PQ), X type zeolite (molecular sieves, 13X, commercially available from Aldrich), and KIT-1, all extruded to form ⅛" as pellet, were each used as a catalyst. The analysis results are given as shown in Table 1, below.

TABLE 1

| Examples | Catalysts | MBA Conversion (%) | PXE Selectivity (%) |
|---|---|---|---|
| Example 3 | Na-Beta | 99.1 | 81.1 |
| Example 4 | Y | 99.9 | 62.5 |
| Example 5 | X | 100 | 57.6 |
| Example 6 | KIT-1 | 100 | 61.4 |

EXAMPLE 7

The same procedure as that of Example 1 was repeated, except that a reactant mixture of xylene and MBA containing 10% acetophenone was reacted for 100 hours in the presence of a modernite catalyst extruded with the aid of 20% alumina. Analysis showed that the MBA conversion and the PXE selectivity were 100.0% and 78.3 wt %, respectively, on the average.

COMPARATIVE EXAMPLES 1 TO 6

To a 250 ml autoclave containing 100 ml of para-xylene, a homogeneous catalyst (AlCl$_3$, SiCl$_4$) or a heterogeneous active clay was added as much as 50 wt % of styrene. Reaction was executed for predetermined times with dropwise addition of styrene. The catalysts used, the reaction conditions and the PXE selectivity are given in Table 2, below.

TABLE 2

| Comparative Examples | Catalysts | Rxn. Temp. (° C.) | Rxn. Time (hour) | PXE Selectivity (%) |
|---|---|---|---|---|
| C. Examp. 1 | AlCl$_3$ | 25 | 20 | 0 |
| C. Examp. 2 | SiCl$_4$ | 25 | 20 | 0 |
| C. Examp. 3 | Active Clay A | 25 | 20 | 0 |
| C. Examp. 4 | Active clay B | 25 | 20 | 0 |
| C. Examp. 5 | Active clay A | 60 | 5 | 20 |
| C. Examp. 6 | Active clay B | 80 | 3 | 80 |

Industrial Applicability

As described hereinbefore, the method according to the present invention enables DAE to be prepared at a low cost in a high production yield, so that it is applicable to commercial processes.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing 1,1-diarylethane, which comprises conducting an alkation reaction in a continuous type process at a temperature of 100–300° C. under a reaction pressure of 1–45 kg/cm$^2$ G in the presence of a solid acid catalyst while a reactant mixture comprising alpha-methylenzylalcohol and at least one aromatic hydrocarbon at a volume ratio of 1:1–10, is fed at a weight hourly space velocity of 0.1–10 h$^{-1}$, said alpha-methylbenzylalcohol acting as an alkylating agent.

2. A method as set forth in claim 1, wherein said aromatic hydrocarbon is selected from the group consisting of benzene, toluene, ortho-xylene, meta-xylene, para-xylene, ethyl benzene, trimethyl benzene and the mixtures thereof.

3. A method as set forth in claim 1, wherein said solid acid catalyst is selected from the group consisting of Y type zeolite, X type zeolite, zeolite beta($\beta$), modernite, L type zeolite, ZSM-5, ZSM- 11, ZSM- 18, ZSM-12, mazzite, offretite, MCM-41, KIT-1, KIT-2, AIKIT-3, clay, and silica-alumina.

4. A method as set forth in claim 1, wherein said alkylation is carried out at a temperature of 120–270° C.

5. A method an set forth in claim 1, wherein said reaction pressure is on the order of 2–40 kg/cm$^2$ G and is maintained by feeding a gas selected from the group consisting of argon (Ar), nitrogen (N$_2$) and hydrogen (H$_2$) and the mixtures thereof.

6. A method as set forth in claim 1, wherein said reactant mixture comprises alpha-methylbenzylalcohol and at least one aromatic hydrocarbon at a volume ratio of 1:2–8.

7. A method as set forth in claim 1, wherein said reactant mixture is fed at a weight hourly space velocity of 2–8 h$^{-1}$.

* * * * *